(12) United States Patent
Woolston et al.

(10) Patent No.: US 7,104,973 B2
(45) Date of Patent: Sep. 12, 2006

(54) MEDICAMENT CARTRIDGE

(75) Inventors: Robert Woolston, Warwick (GB); Christopher Nigel Langley, Warwickshire (GB); Lee Simon Adams, Warwick (GB)

(73) Assignee: DCA Design International Limited, Warwick (GB)

( * ) Notice: Subject to any disclaimer, the term of this patent is extended or adjusted under 35 U.S.C. 154(b) by 0 days.

(21) Appl. No.: 11/151,209

(22) Filed: Jun. 14, 2005

(65) Prior Publication Data

US 2006/0106344 A1   May 18, 2006

Related U.S. Application Data

(63) Continuation of application No. 10/307,302, filed on Dec. 2, 2002, now abandoned.

(30) Foreign Application Priority Data

Dec. 6, 2001   (GB) ................................. 0129187.1

(51) Int. Cl.
  *A61B 19/00*   (2006.01)
  *A61M 37/00*   (2006.01)
(52) U.S. Cl. ...................... 604/232; 604/131
(58) Field of Classification Search ................ 604/232, 604/131; 128/DIG. 12
  See application file for complete search history.

(56) References Cited

U.S. PATENT DOCUMENTS

| 5,456,670 | A | * | 10/1995 | Neer et al. ................... 604/155 |
| 5,800,397 | A | * | 9/1998 | Wilson et al. ............... 604/151 |
| 6,110,152 | A | | 8/2000 | Kovelman |
| 6,475,192 | B1 | | 11/2002 | Reilly et al. |
| 2001/0041869 | A1 | * | 11/2001 | Causey et al. ............... 604/152 |
| 2002/0020654 | A1 | | 2/2002 | Eilersen |
| 2002/0134377 | A1 | | 9/2002 | Loeffler et al. |
| 2003/0006209 | A1 | * | 1/2003 | Stefen et al. ................ 215/386 |
| 2003/0065287 | A1 | | 4/2003 | Spohn et al. |
| 2004/0064101 | A1 | * | 4/2004 | Kowan et al. ............... 604/189 |

FOREIGN PATENT DOCUMENTS

| EP | 0 747 075 A2 | 12/1996 |
| EP | 0 829 268 A2 | 3/1998 |
| WO | WO 95/13841 | 5/1995 |
| WO | WO 01/56635 A1 | 8/2001 |

* cited by examiner

*Primary Examiner*—Sharon Kennedy
(74) *Attorney, Agent, or Firm*—Oliff & Berridge, PLC

(57) ABSTRACT

Many of those having diabetes take a combination of slow and fast acting types of insulin. It is important that the different forms of medicament do not become confused and that the patient does not receive the incorrect medicament. In combination a medicament delivery apparatus and a medicament cartridge are provided, the medicament delivery apparatus including at least one switch and the medicament cartridge comprising a cartridge housing within which a medicament is provided, a displaceable piston located internally at one end of the housing and a raised ring of material about an external periphery of the medicament cartridge, the ring of material being of sufficient dimensions, in use, to trip the at least one switch of the medicament delivery apparatus.

6 Claims, 2 Drawing Sheets

US 7,104,973 B2

MEDICAMENT CARTRIDGE

This is a Continuation of application Ser. No. 10/307,302 filed Dec 2, 2002 now abandoned. The entire disclosure of the prior application is hereby incorporated by reference herein.

BACKGROUND

The present invention relates to a medicament cartridge, having particular, but not exclusive application for use with a medication delivery apparatus. The invention provides a medication cartridge that maybe dedicated to a particular medication delivery apparatus. A medication delivery apparatus may take the form of for example, an injector pen or an infuses apparatus.

It is known that a person providing themselves, or others, with a medicament regimen may require more than one medicament as part of that regime. For example many of those having diabetes take a combination of slow and fast acting types of insulin. It is important that the different forms of medicament do not become confused and that the patient does not receive the incorrect medicament By providing a cartridge that can be dedicated to a particular form of medicament, this problem may be eliminated or at least substantially reduced. For example, such a cartridge may only be accepted by a certain medication delivery apparatus or might not permit the proper functioning of certain medication delivery apparatus.

SUMMARY

According to the present invention, in combination a medicament delivery apparatus and a medicament cartridge are provided, the medicament delivery apparatus including at least one switch and the medicament cartridge comprising a cartridge housing within which a medicament is provided, a displaceable piston located internally at one end of the housing and a raised ring of material about an external periphery of the medicament cartridge, the ring of material being of sufficient dimensions, in use, to trip the at least one switch of the medicament delivery apparatus.

Preferably a location of the raised ring of material along a longitudinal axis of the cartridge housing provides an indication of the medicament contained within the medicament cartridge.

Preferably the raised ring of material may be colour coded to provide an indication of the medicament contained within the medicament cartridge.

Preferably the raised ring of material is defined by a first inner surface that conforms to a peripheral surface of the cartridge and a second outer surface. More preferably, the second outer surface provides a smooth rounded surface. Advantageously, a shape of the outer surface of the raised ring of material provides an indication of the medicament contained within the medicament cartridge.

Preferably the medication delivery apparatus further comprises a display, the processor causing the display to show information relating to the medicament cartridge within the medication delivery apparatus.

Preferably unless the at least one switch is tripped the medication delivery apparatus will not function.

BRIEF DESCRIPTION OF THE DRAWINGS

The invention will now be described, by way of example only, with reference to the accompanying drawings in which.

DETAILED DESCRIPTION OF EMBODIMENTS

Figure 1:
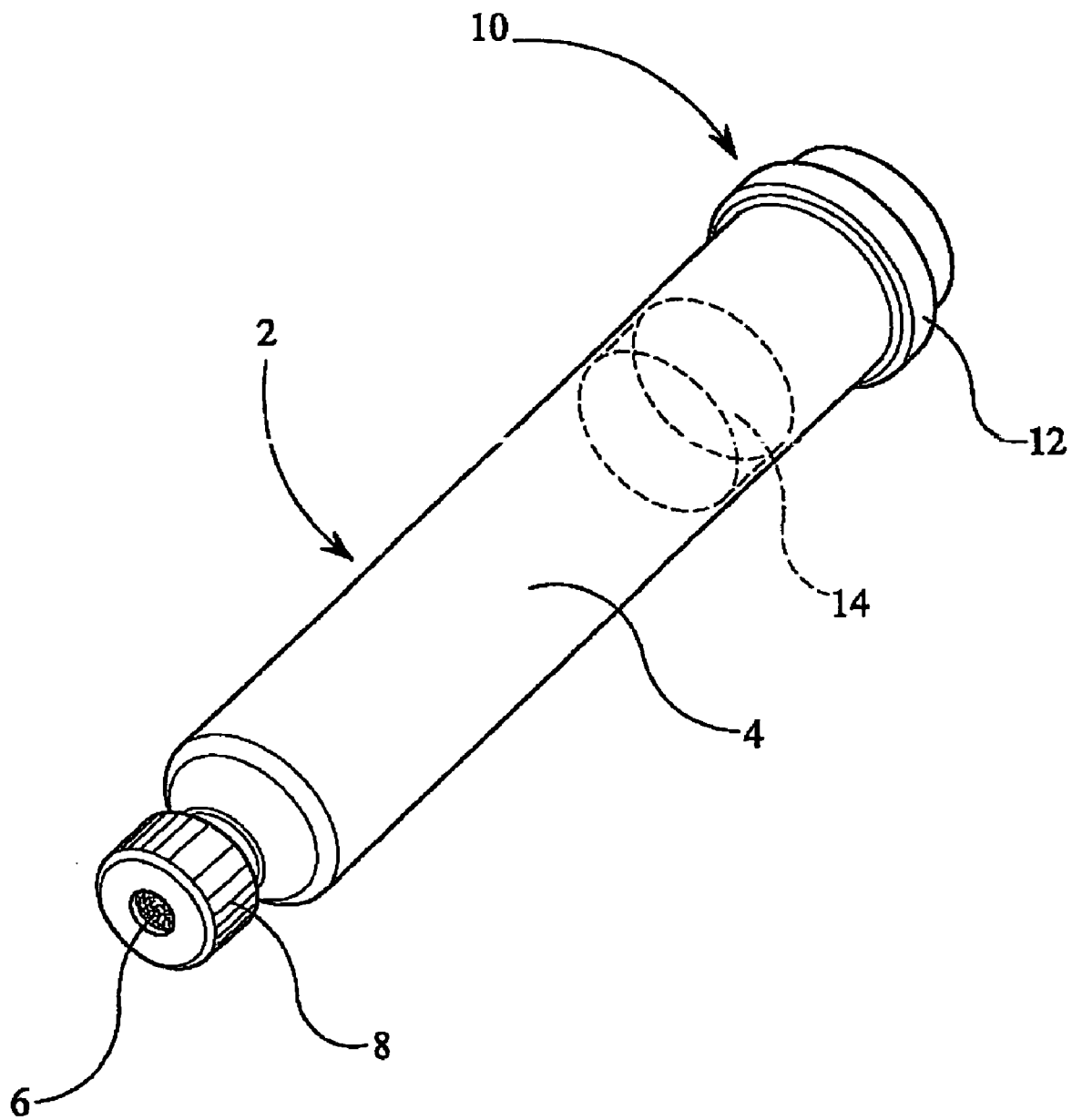
FIG. 1 shows a medicament cartridge in accordance with the first aspect of the invention.

Referring to FIG. 1, there may be seen a medicament cartridge 2 in accordance with the present invention.

The medicament cartridge comprises a cartridge housing 4 having an open neck at a first end. The open neck is provided with an external flange. A flexible fluid impermeable membrane 6 is sealingly secured across the neck by a cap 8 secured against the flange. The metal cap 8 has a central opening through which the membrane 6 is exposed. In use, a needle of a needle unit penetrates the membrane 6.

The medicament is contained within a chamber defined by the cartridge housing 4, the flexible membrane 6 at the first end of the cartridge housing and a displaceable piston 14 (shown in ghost) located at a second end of the cartridge housing 4. Movement of the piston 14 towards the first end of the cartridge housing 4 causes the medicament to be dispensed through the needle unit.

The medicament cartridge of the present invention is additionally provided with a raised ring 10 of material about an external periphery of the cartridge housing 4. The raised ring 10 of material may be formed of any suitable material by any suitable method.

In the illustrated embodiment, the raised ring 10 of material is defined by a first inner surface that conforms to a peripheral surface of the cartridge housing 4 and a second outer surface 12. In the illustrated embodiment, the raised ring 10 is of generally rectangular section. The second outer surface 12 is shown as a smooth rounded surface. The raised ring 10 may be forward as a moulding of a plastics material about the cartridge housing 4. This may occur prior to filling or loading of the medicament cartridge with medicament. In such a case the location of the raised ring 10 may be used during the filling or loading operation to ensure that the medicament cartridge receives the correct medicament.

Since location of the raised ring 10 is determined during manufacture, and as such is a highly repeatable operation, the location of the raised ring 10 may be used as an indication of the medicament contained within the medicament cartridge.

Figure 2:
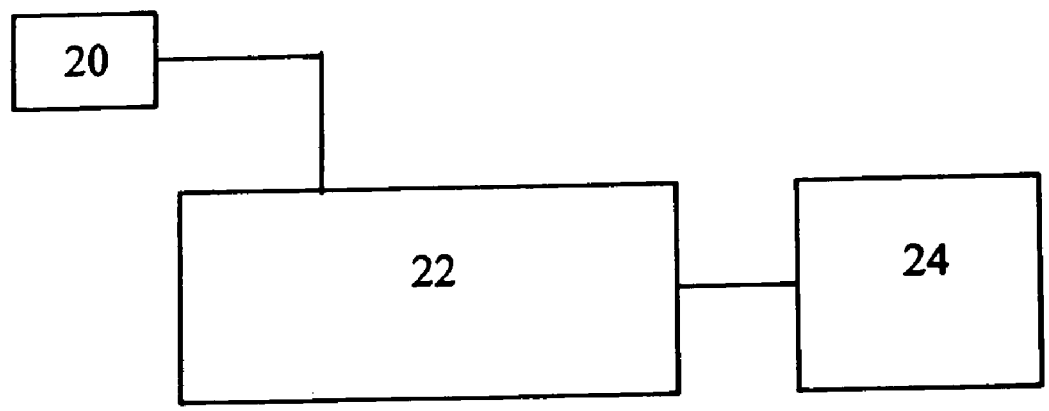
FIG. 2 shows schematically a part of a first medication delivery apparatus for use with a medicament cartridge in accordance with the first aspect of the invention.
Figure 3:
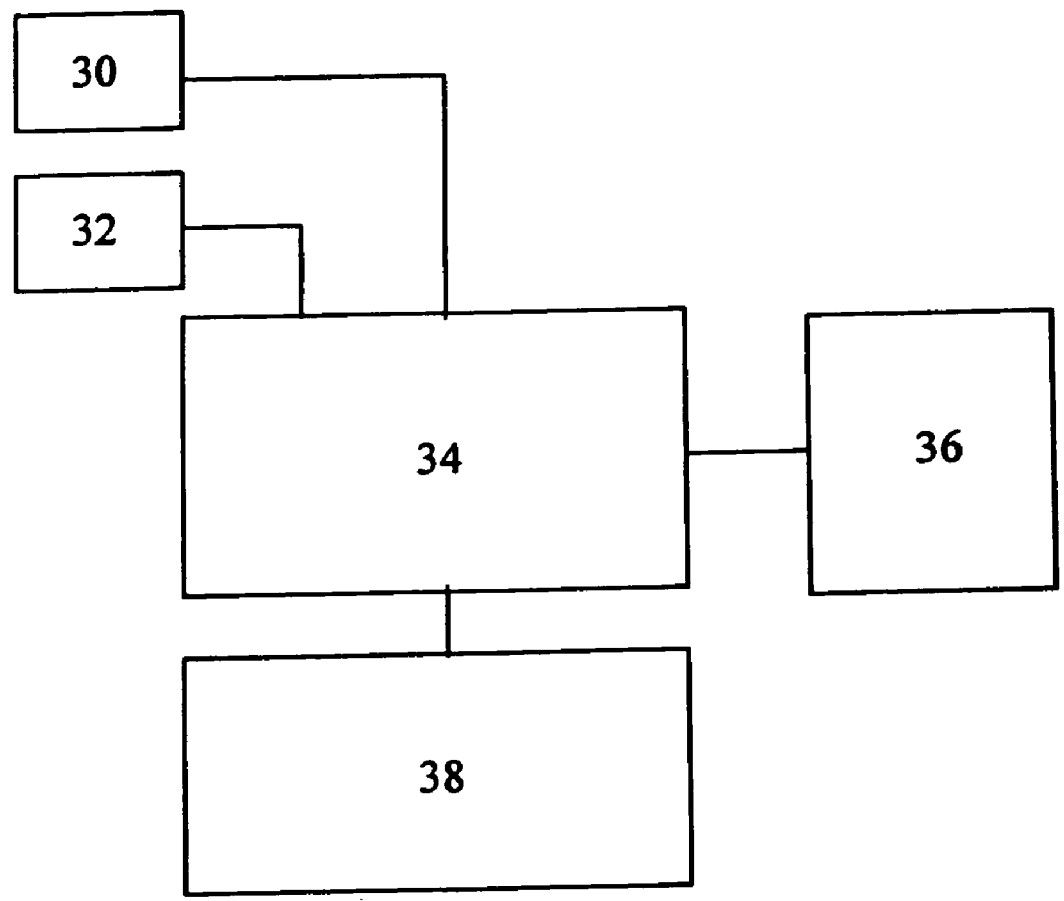
FIG. 3 shows schematically a part of a second medication delivery apparatus for use with a medicament cartridge in accordance with the first aspect of the invention

Thus, a medicament delivery apparatus (FIG. 2) maybe provided with a processor 22 and a switch 20. When the switch 20 is tripped this allows the medicament delivery apparatus to function. If the switch 20 is not tripped, either because there is no raised ring 10 present, or is present at an incorrect location along a longitudinal axis of the medicament cartridge inserted, such a medicament delivery apparatus will not operate.

Alternatively, a medication delivery apparatus may comprise a processor 34 and a plurality of switches 30,32, tripping of a particular switch indicating the presence of a medicament cartridge containing a particular medicament within the medication delivery apparatus. The medication delivery apparatus may further comprise a display 36, the processor 34 causing the display to show information relating to the medicament cartridge within the medication delivery apparatus, for example whether the medicament is a fast acting or slow acting form of medicament. This has the advantage that it provides a user with an additional opportunity to check that the correct medicament is to be dispensed. Optionally, the processor 34 may actuate a drive mechanism 38 to express medicament from the cartridge 2.

It will be understood that quite small differences in location may be enough to enable a medication delivery apparatus to distinguish between medicament cartridges having differing contents. However, such differences may not be readily apparent to all users of the cartridges, for example those with impaired vision. For this reason, the raised ring 10 may also be formed of a material of a particular colour to indicate a particular medicament within a medicament cartridge. Alternatively, or additionally, the raised ring 10 may also be formed in a particular shape to indicate a particular medicament within a medicament cartridge. This may be of particular advantage to those having more seriously impaired vision.

What is claimed is:

1. In combination a medicament delivery apparatus and a medicament cartridge, the medicament delivery apparatus including at least one switch and the medicament cartridge comprising a cartridge housing within which a medicament is provided, a displaceable piston located internally at one end of the housing and a raised ring of material about an external periphery of the medicament cartridge, the ring of material being of sufficient dimensions, in use, to trip the at least one switch of the medication delivery apparatus, wherein the location of the raised ring of material along a longitudinal axis of the cartridge housing provides an indication of the medicament contained within the medicament cartridge, and said medication delivery apparatus further comprises a display, and a processor causing the display to show information relating to the medicament cartridge within the medication delivery apparatus.

2. The combination of claim 1, in which the raised ring of material may be colour coded to provide an indication of the medicament contained within the medicament cartridge.

3. The combination of claim 1, in which the raised ring of material is defined by a first inner surface that conforms to a peripheral surface of the cartridge and a second outer surface.

4. The combination of claim 3, in which the second outer surface provides a smooth rounded surface.

5. The combination of claim 3, in which a shape of the outer surface oldie raised ring of material provides an indication of the medicament contained within the medicament cartridge.

6. The combination of claim 1, in which unless the at least one switch is tripped the medication delivery apparatus will not function.

\* \* \* \* \*